United States Patent [19]

Maeda et al.

[11] Patent Number: 4,965,404
[45] Date of Patent: Oct. 23, 1990

[54] PROCESS FOR THE PREPARATION OF LITHIUM DIPHENYLPHOSPHINOBENZENE-M-MONOSULFONATE

[75] Inventors: Toshihiko Maeda, Kanagawa; Noriaki Yoshimura, Okayama, both of Japan

[73] Assignee: Kuraray Company, Ltd., Kurashiki, Japan

[21] Appl. No.: 483,828

[22] Filed: Feb. 23, 1990

[30] Foreign Application Priority Data

Mar. 9, 1989 [JP] Japan .................................. 1-58225

[51] Int. Cl.$^5$ ........................................... C07C 307/00
[52] U.S. Cl. ...................................................... 562/35
[58] Field of Search ........................ 562/35, 45, 97, 76

[56] References Cited

U.S. PATENT DOCUMENTS

| | | | |
|---|---|---|---|
| 4,142,060 | 2/1979 | Kuntz | 562/35 |
| 4,483,802 | 11/1984 | Gartner | 562/35 |
| 4,623,490 | 11/1986 | Bexten | 562/35 |
| 4,654,176 | 3/1987 | Dang | 562/35 |

*Primary Examiner*—Alan Siegel
*Attorney, Agent, or Firm*—Oblon, Spivak, McClelland, Maier & Neustadt

[57] ABSTRACT

There is provided an industrial process for the advantageous preparation of high-purity lithium diphenylphosphinobenzene-m-monosulfonate.

3 Claims, No Drawings

4,965,404

PROCESS FOR THE PREPARATION OF LITHIUM DIPHENYLPHOSPHINOBENZENE-M-MONOSULFONATE

BACKGROUND OF THE INVENTION

1. Field of the Invention

This invention relates to a process for the preparation of lithium diphenylphosphinobenzene-m-monosulfonate.

2. Description of Prior Art

Japanese Patent Application Laid-open KOKAI No. 58-131994 discloses a process for the preparation of lithium diphenylphosphinobenzene-m-monosulfonate which comprises sulfonating triphenylphosphine, extracting the products with 4-methyl-2-pentanone, neutralizing and extracting the same products with an aqueous solution of lithium hydroxide, and evaporating the resulting aqueous layer to recover lithium diphenylphosphinobenzene-m-monosulfonate.

U.S. Pat. No. 4,483,802 discloses a process for the preparation of diphenylphosphinobenzene-m-monosulfonate which comprises sulfonating triphenylphosphine to form a sulfonation mixture, diluting said mixture with water to form an aqueous solution, extracting said aqueous solution with an organic solution of a water-insoluble amine in a water-insoluble organic solvent, separating the resulting organic solution, mixing said organic solution with an aqueous solution of a base to form a basic aqueous layer, separating said basic aqueous layer and recovering diphenylphosphinobenzene-m-monosulfonate.

U.S. Pat. No. 4,142,060 describes a process for the preparation of a salt of tri(m-sulfophenyl) phosphine which comprises treating an aqueous solution of sodium tri(m-sulfophenyl) phosphine with a strongly acidic cation exchange resin, eluting the products with water, reacting the formed acidic aqueous solution with a base to form the other salt of tri(m-sulfophenyl)phosphine.

The problem which arises during carrying out the process for isolating the product from the sulfonation mixture by extraction is the contamination with lithium sulfate in the neutralized aqueous solution because sulfuric acid is simultaneously extracted in the aqueous solution. According to the process using ion exchange resin, the obtained product is colored in the ion exchange reaction. And this process is uneconomic due to tedious procedures such as conversion procedure of the product to its free acid. Lithium diphenylphosphinobenzene-m-monosulfonate cannot be recrystallized from an aqueous solution because of its high solubility in water, the solubility being quite different from that of sodium diphenylphosphinobenzene-m-monosulfonate.

In a catalytic reaction using a noble metal complex, lithium diphenylphosphinobenzene-m-monosulfonate used as a ligand is required to be in high purity.

Consequently, an industrial process for advantageously producing lithium diphenylphosphinobenzene-m-monosulfonate is required.

SUMMARY OF THE INVENTION

It is an object of the invention to provide an industrial process for the advantageous preparation of high-purity lithium diphenylphosphinobenzene-m-monosulfonate.

This object as well as other objects and advantages of the invention will become apparent to those skilled in the art from the following detailed description.

In order to accomplish the foregoing objects according to the invention, there is provided a process for the preparation of lithium diphenylphosphinobenzene-m-monosulfonate which comprises reacting at least one of sodium salt, potassium salt and calcium salt of diphenylphosphinobenzene-m-monosulfonic acid (herinafter referred to as "sodium diphenylphosphinobenzene-m-monosulfonate and the like") with lithium sulfate in an organic solvent.

DESCRIPTION OF THE PREFERRED EMBODIMENTS

Sodium diphenylphosphinobenzene-m-monosulfonate and the like used in the invention is desired to have a purity of 99% or more, and can be easily obtained by well known processes (cf. Japanese Patent Application Laid-open KOKAI No. 58-131994).

The amount of lithium sulfate to be used is 1 to 50 mole equivalents, preferably 1 to 5 mole equivalents of sodium diphenylphosphinobenzene-m-monosulfonate and the like.

The organic solvents to be used in the invention are those which do not dissolve lithium sulfate and dissolve both sodium diphenylphosphinobenzene-m-monosulfonate and the like and lithium diphenylphosphinobenzene-m-monosulfonate. Particularly suitable organic solvents are alcohols such as methanol, ethanol, propanol, isopropanol, butanol and the like; nitriles such as acetonitrile and the like; ethers such as tetrahydrofuran, dioxane and the like; ketones such as acetone, methyl ethyl ketone, methyl isobutyl ketone and the like. These solvents may be used either singly or in combination. Among these organic solvents, alcohols, are particularly preferable in view of solubility. These solvents are used in an amount of at least dissolving lithium diphenylphosphinobenzene-m-monosulfonate at room temperature, more practically in such an amount that the concentration of lithium diphenylphosphinobenzene-m-monosulfonate is 1 to 0.01 mol/liter depending upon the solubility of the solvent.

The ion exchange reaction in the invention is carried out at a temperature of room temperature of 150° C., preferably about $\alpha$° C. to about 120° C. With an increase in the reaction temperature, the reaction rate increases, but the purity of lithium diphenylphosphinobenzene-m-monosulfonate obtained lowers at more than 150° C. The ion exchange reaction is conducted in an atmosphere of inert gas such as nitrogen, argon and the like. In the ion exchange reaction, the condition which allows to stand satisfactory solid-liquid contact increases the reaction efficiency. As a reactor may be used a vessel with a stirrer or a reactor with fixed beds.

The isolation of lithium diphenylphosphinobenzene-m-monosulfonate from the reaction mixture is carried out in the following ways. After the completion of reaction, inorganic salts are removed by filtration. Then, lithium diphenylphosphinobenzene-m-monosulfonate is isolated from the mother liquor by distilling off the organic solvents or by filtering off the precipitate which is yielded by adding a hydrocarbon solvent having poor solubility to lithium diphenylphosphinobenzene-m-monosulfonate such as pentane, hexane, benzene, toluene, xylene and the like into the mother liquor. Thus isolated lithium diphenylphosphinobenzene-m-monosulfate is dried under reduced pressure to give anhydride, monohydrate, dihydrate or the mixtures thereof.

Metal salts of diphenylphosphinobenzene-m-monosulfonic acid such as lithium diphenylphosphinobenzene-m-monosulfonate, which are water-soluble trisubstituted phosphines, stabilize or modify the activities of metallic catalysts in various catalytic reactions. Also the salts which are capable of dissolving catalytic components in solvents containing water provide a process isolating the catalyst from slightly water-soluble products by decantation or extraction at room temperature without applying the solution containing the catalysts to distillation which tends to thermally degrade the catalysts. These features make the salts to be industrially important compounds.

Also Japanese Patent Application Laid-open KOKAI No. 58-131994 describes that lithium diphenylphosphinobenzene-m-monosulfonate has a much higher water-solubility than that of the corresponding sodium or potassium salt. In the reaction using a metallic catalyst, using metal salts of diphenylphosphinobenzene-m-monosulfonic acid as much as possible is desireable to prevent the deactivation of the metallic catalysts as caused by metalation etc. For such purpose, lithium diphenylphosphinobenzene-m-monosulfonate is particularly useful.

According to the present invention, it has been possible to produce lithium diphenylphosphinobenzene-m-monosulfonate in high purity.

EXAMPLES

Other features of the invention will become apparent in the course of the following descriptions of exemplary embodiments which are given for illustration of the invention and are not intended to be limiting thereof.

REFERENCE EXAMPLE 1

Synthesis of Sodium Diphenylphosphinobenzene-M-Monosulfonate

A 500-ml four-necked flask equipped with thermometer, stirrer, dropping funnel and nitrogen gas inlet and outlet was charged with 80 g of triphenylphosphine and 36 g of concentrated sulfuric acid after replacing the atmosphere with nitrogen gas and the reaction was conducted maintaining the inside temperature at 30° C. or less. To the reaction mixture was added dropwise 320 g of fuming sulfuric acid containing 20% by weight of $SO_3$ with stirring over a period 30 minutes maintaining the inside temperature at 30° C. or less. After completion of adding fuming sulfuric acid, stirring was continued for 3 additional hours. Analysis of unreacted triphenylphosphine in the reaction mixture by liquid chromatography revealed conversion rate of triphenylphosphine of 60%. About 1500 ml of ice-cold water was added to the reaction mixture under cooling to give an aqueous solution of sulfuric acid in concentration of about 20%. This aqueous solution of sulfuric acid was extracted twice each with 700 ml of 4-methyl-2-pentanone. The 4-methyl-2-pentanone layer was neutralized with about 150 ml of about 4 wt % aqueous solution of sodium hydroxide. When the settled aqueous layer was cooled to 15° C., white crystalline precipitate was separated. The crystalline precipitate was collected by filtration. The collected crystalline precipitate was recrystallized twice from distilled water. Finally 45 g of sodium diphenylphosphinobenzene-m-monosulfonate dihydrate was obtained. It was revealed by the analyses of elemental analysis, ion chromatography, liquid chromatography, etc. that the obtained sodium diphenylphosphinobenzene-m-monosulfate dihydrate had a purity of 100%.

EXAMPLE 1

A one-liter three-necked flask equipped with stirrer, reflux condenser and nitrogen gas inlet and outlet was charged under nitrogen atmosphere with 250 ml of methanol, 250 ml of isopropanol, and 151 g of sodium diphenylphosphinobenzene-m-monosulfate dihydrate obtained in Reference Example 1, thereafter 48 g of lithium sulfate monohydrate. The mixture was refluxed for 6 hours with stirring. After completion of the reaction, inorganic salts were removed by filtration. To the obtained mother liquor was added 250 ml of toluene, thereafter methanol and isopropanol were distilled off to replace the solvent with toluene. Precipitated crystalline of lithium diphenylphosphinobenzene-m-monosulfonate was isolated by filtration. The collected lithium diphenylphosphinobenzene-m-monosulfonate was dried at 150° C. under reduced pressure of 5 mmHg for 4 hours to give 128 g of lithium diphenylphosphinobenzene-m-monosulfonate. It was revealed by the analyses of elemental analysis, ion chromatography, liquid chromatography, etc. that the obtained lithium diphenylphosphinobenzene-m-monosulfonate had a purity of 100%.

EXAMPLE 2

The same reaction setup as used in Example 1 was charged with 151 g of sodium diphenylphosphinobenzene-m-monosulfonate dihydrate obtained in Reference Example 1, 48 g of lithium sulfate monohydrate and 2 liters of dioxane. The mixture was refluxed for 8 hours with stirring. After completion of the reaction, inorganic salts were removed by filtration. After almost of dioxane was removed from mother liquor using an evaporator, the residue was dried at 150° C. under reduced pressure of 5 mmHg for 4 hours to give 130 g of lithium diphenylphosphinobenzene-m-monosulfonate. It was revealed by the analyses of elemental analysis, ion chromatography, liquid chromatography, etc. that the obtained lithium diphenylphosphinobenzene-m-monosulfonate had a purity of 100%.

EXAMPLE 3

The same reaction setup as used in Example 1 was charged with 151 g of sodium diphenylphosphinobenzene-m-monosulfonate dihydrate obtained in Reference Example 1, 48 g of lithium sulfate monohydrate and 4 liters of 4-methyl-2-pentanone. The mixture was refluxed for 8 hours with stirring. After completion of the reaction, inorganic salts were removed by filtration. After almost of 4-methyl-2-pentanone was removed from mother liquor using an evaporator, the residue was dried at 150° C. under reduced pressure of 5 mmHg for 4 hours to give 130 g of lithium diphenylphosphinobenzene-m-monosulfonate. It was revealed by the analyses of elemental analysis, ion chromatography, liquid chromatography, etc. that the obtained lithium diphenylphosphinobenzene-m-monosulfonate had a purity of 100%.

REFERENCE EXAMPLE 2

Synthesis of Potassium Diphenylphosphinobenzene-M-Monosulfonate

A 500-ml four-necked flask equipped with thermometer, stirrer, dropping funnel and nitrogen gas inlet and outlet was charged with 80 g of triphenylphosphine and 36 g of concentrated sulfuric acid after replacing the atmosphere with nitrogen gas and the reaction was conducted maintaining the inside temperature at 30° C. or less. To the reaction mixture was added dropwise 320 g of fuming sulfuric acid containing 20% by weight of SO$_3$ with stirring over a period of 30 minutes maintaining the inside temperature at 30° C. or less. After completion of adding fuming sulfuric acid, stirring was continued for 2.75 additional hours. Analysis of unreacted triphenylphosphine in the reaction mixture by liquid chromatography revealed conversion rate of triphenylphosphine of 45%. About 1500 ml of ice-cold water was added to the reaction mixture under cooling to give an aqueous solution of sulfuric acid in concentration of about 20%. This aqueous solution of sulfuric acid was extracted twice each with 700 ml of 4-methyl-2-pentanone. The 4-methyl-2-pentanone layer was neutralized with about 5 wt % aqueous solution of potassium carbonate. When the settled aqueous layer was cooled to 15° C., white crystalline precipitate was separated and collected by filtration. The collected crystalline precipitate was recrystallized twice from the solution dissolved in distilled water. Finally 43 g of potassium diphenylphosphinobenzene-m-monosulfonate dihydrate was obtained. It was revealed by the analyses of elemental analysis, ion chromatography, liquid chromatography, etc. that the obtained potassium diphenylphosphinobenzene-m-monosulfonate dihydrate had a purity of 100%.

EXAMPLE 4

A one-liter three-necked flask equipped with stirrer, reflux condenser and nitrogen gas inlet and outlet was charged under nitrogen atmosphere with 250 ml of methanol, 250 ml of isopropanol and 157 g of potassium diphenylphosphinobenzene-m-monosulfonate dihydrate obtained in Reference Example 2, thereafter 48 g of lithium sulfate monohydrate. The mixture was refluxed for 6 hours with stirring. After completion of the reaction, inorganic salts were removed by filtration. To the obtained mother liquor was added 250 ml of toluene, thereafter methanol and isopropanol were distilled off to replace the solvent with toluene. Precipitated crystalline of lithium diphenylphosphinobenzene-m-monosulfonate was isolated by filtration. The collected lithium diphenylphosphinobenzene-m-monosulfonate was dried at 150° C. under reduced pressure of 5 mmHg for 4 hours to give 128 g lithium diphenylphosphinobenzene-m-monosulfonate. It was revealed by the analyses of elemental analysis, ion chromatography, liquid chromatography, etc. that the obtained lithium diphenylphosphinobenzene-m-monosulfonate had a purity of 100%.

COMPARATIVE EXAMPLE 1

Using the same reaction setup as used in Reference Example 1 and repeating the procedures of Reference Example 1, the sulfonation reaction of triphenylphosphine was carried out, and the reaction mixture was extracted with 4-methyl-2-pentanone. The 4-methyl-2-pentanone layer was neutralized with about 4 wt % aqueous solution of lithium hydroxide. The aqueous layer was separated, and from this aqueous layer was removed almost of water using an evaporator. To the residue was added 400 ml of 4-methyl-2-pentanone, and the water remained in the residue was removed by azeotropic distillation to give 40 g of white precipitate. It was revealed by the analyses of elemental analysis, ion chromatography, liquid chromatography, etc. that the obtained precipitate consisted of 0.5 wt % of lithium sulfate, 2.0 wt % of the oxide of lithium diphenylphosphinobenzene-m-monosulfonate, 95 wt % of lithium diphenylphosphinobenzene-m-monosulfonate and 2.5 wt % of lithium disulfonate.

COMPARATIVE EXAMPLE 2

The same reaction setup as used in Example 1 was charged with 151 g sodium diphenylphosphinobenzene-m-monosulfonate dihydrate obtained in Reference Example 1, 200 g (total ion-exchange capacity: 0.88 gram equivalent) of Amberlyst 15 ® (manufactured by Rohm and Haas Company in U.S.A.) and 600 ml of butanol. The mixture was refluxed for 8 hours with mild stirring. After completion of the reaction, the ion-exchange resin was removed by filtration. The obtained mother liquor was colored in brown. The mother liquor was neutralized with an aqueous solution of lithium hydroxide. After almost of water was removed from the aqueous layer by distillation using an evaporator, the residue was dried at 150° C. under reduced pressure of 5 mmHg for 4 hours to give 130 g of lithium diphenylphosphinobenzene-m-monosulfonate colored in brown.

The same procedures were repeated except that lithium sulfonate type ion-exchange resin as obtained by supplying lithium cation to Amberlyst 15 ® by a common method was used in lieu of Amberlyst 15 ®, and the mixture was refluxed for 8 hours with mild stirring. After completion of the reaction, the ion-exchange resin was removed by filtration. From the obtained mother liquor as removed almost of butanol using an evaporator. The residue was dried at 150° C. under reduced pressure of 5 mmHg for 4 hours to give 130 g of lithium diphenylphosphinobenzene-m-monosulfonate colored in brown.

We claim:

1. A process for the preparation of lithium diphenylphosphinobenzene-m-monosulfonate which comprises reacting at least one of sodium salt, potassium salt and calcium salt of diphenylphosphinobenzene-m-monosulfonic acid with lithium sulfate in an organic solvent.

2. The process as defined in claim 1, wherein said sodium salt, potassium salt and calcium salt of diphenylphosphinobenzene-m-monosulfonic acid are of purity of 99% or more.

3. The process as defined in claim 1, wherein said organic solvent is an alcohol.

* * * * *